US010197481B2

(12) United States Patent
Gahlawat et al.

(10) Patent No.: US 10,197,481 B2
(45) Date of Patent: Feb. 5, 2019

(54) OPTICAL MEASUREMENT SYSTEM

(71) Applicant: Halliburton Energy Services, Inc., Houston, TX (US)

(72) Inventors: Ravinder Gahlawat, Pune (IN); Abhinandan Chiney, Pune (IN); Sameer Bardapurkar, Pune (IN); Siva Rama Krishna Jandhyala, Pune (IN)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 15/543,129

(22) PCT Filed: Mar. 2, 2015

(86) PCT No.: PCT/US2015/018346
§ 371 (c)(1),
(2) Date: Jul. 12, 2017

(87) PCT Pub. No.: WO2016/140648
PCT Pub. Date: Sep. 9, 2016

(65) Prior Publication Data
US 2018/0010992 A1    Jan. 11, 2018

(51) Int. Cl.
*G01N 3/00* (2006.01)
*G01N 3/08* (2006.01)
*G01N 33/38* (2006.01)
*G01B 11/16* (2006.01)

(52) U.S. Cl.
CPC ............... *G01N 3/08* (2013.01); *G01B 11/16* (2013.01); *G01N 33/383* (2013.01)

(58) Field of Classification Search
CPC ......... G01N 3/08; G01N 33/383; G01B 11/16

USPC .......................................................... 73/800
See application file for complete search history.

(56) References Cited

U.S. PATENT DOCUMENTS

| 6,817,238 | B2 | 11/2004 | Go Boncan et al. |
| 7,224,475 | B2 | 5/2007 | Robertson et al. |
| 8,949,067 | B1 | 2/2015 | Hammar et al. |
| 9,074,468 | B1 * | 7/2015 | Selman ................ E21B 47/122 |
| 2006/0146345 | A1 | 7/2006 | Robertson et al. |
| 2006/0170934 | A1 | 8/2006 | Picciotto et al. |

(Continued)

FOREIGN PATENT DOCUMENTS

| EP | 1333267 | 8/2003 |
| KR | 101413721 | 7/2014 |

OTHER PUBLICATIONS

International Search Report and Written Opinion of PCT Application No. PCT/US2015/018346 dated Oct. 30, 2015: pp. 1-13.

(Continued)

*Primary Examiner* — Max H Noori
(74) *Attorney, Agent, or Firm* — Chamberlain Hrdlicka

(57) ABSTRACT

An optical measurement system comprising a vessel for non-invasively testing a sample material composition in-situ and in real time. The test chamber is configured to hold a sample material composition for a wellbore. The optical measurement system is configured to provide in-situ monitoring of the sample material composition in real time and at high temperature and high pressure. Dimensional and geometrical changes occurring within the sample material composition are monitored using the optical measurement system. The system further performs goniometry on a sample.

20 Claims, 4 Drawing Sheets

(56) References Cited

U.S. PATENT DOCUMENTS

| | | | |
|---|---|---|---|
| 2007/0137285 A1 | 6/2007 | Jennings | |
| 2007/0137896 A1* | 6/2007 | Villareal | E21B 17/16 175/59 |
| 2009/0159334 A1* | 6/2009 | Alberty | E21B 21/08 175/40 |
| 2017/0212262 A1* | 7/2017 | Yao | G01V 1/50 |

OTHER PUBLICATIONS

Anonymous, "Recommended Practice on Determination of Shrinkage and Expansion of Well Cement Formulations at Atmospheric Pressure," American Petroleum Institute, ANSI/API Recommended Practice 10B-5, First Edition, Apr. 2005: 1-24.

Backe et al., "Shrinkage of Oil Well Cement Slurries," JCPT, Sep. 1998, vol. 37(9): pp. 63-67.

Beirute et al., "Expansive and Shrinkage Characteristics of Cements Under Actual Well Conditions," Journal of Petroleum Technology, Aug. 1973: pp. 905-909.

Cheneveret et al., "Chemical Shrinkage Properties of Oilfield Cements," SPE Drilling Engineering, Mar. 1991: pp. 37-43.

Ghofrani et al., SPE/IADC 25697: "CaO- and/or MgO-Swelling ments: A Key for Providing a Better Annular Sealing?" Society of Petroleum Engineers, 1993: pp. 199-214.

Goboncan et al., SPE/IADC 79911: "Real-Time Cement Expansion/ Shrinkage Testing Under Downhole Conditions Enhanced Annular Isolation," Society of Petroleum Engineers, 2003: pp. 1-9.

Reddy et al., "Cement-Shrinkage Measurement in Oilwell Cementing—A Comparative Study of Laboratory Methods and Procedures." SPE Drilling & Completion, Mar. 2009: pp. 104-114.

Ahuja et al., "Optical sensors and their applications," Journal of Scientific Research and Reviews, Nov. 2012, vol. 1(5): pp. 060-068, <https://pdfs.semanticscholar.org/9d64/ 240abbe54d7147a56fa5d660f69dcc0a632b.pdf>.

* cited by examiner

OPTICAL MEASUREMENT SYSTEM

BACKGROUND

This section is intended to introduce the reader to various aspects of art that may be related to various aspects of the presently described embodiments. This discussion is believed to be helpful in providing the reader with background information to facilitate a better understanding of the various aspects of the present embodiments. Accordingly, it should be understood that these statements are to be read in this light, and not as admissions of prior art.

This disclosure generally relates to a real-time, in-situ, and non-invasive laboratory apparatus and method for evaluating the performance and design of materials for use in a wellbore, such as cement and drilling fluids.

Oil and gas wells extend from the surface to one or more subterranean formations of rock containing oil and/or gas. The well is typically cased by cementing a steel or other suitable casing in the wellbore. The casing stabilizes the sides of the wellbore, prevents pollution of fresh water reservoirs, and/or prevents fluids from zones other than oil and gas producing zones from entering the wellbore.

When cementing casing, wet cement slurry is pumped down the wellbore to fill the annular space defined between the casing and the rock walls. The cement protects the casing and prevents water and other fluids from entering the space between the casing and rock walls of the wellbore. Cement volume change due to hydration is an important consideration for engineers designing and supervising the cement slurry. Failure to account for changes in cement volume (i.e., shrinkage or expansion) may lead to debonding and in some cases failure of the cement sheath, leading to a loss of zonal isolation. Laboratory technicians test and select the cement slurry and additives to optimize cement performance at particular downhole conditions.

When drilling a well, a drilling fluid (e.g., drilling mud) is pumped down the drill string to facilitate the drilling process, including suspending cuttings generated during drilling, controlling pressure in the wellbore, stabilizing exposed formation, providing buoyancy, and cooling and lubricating the drill bit. Over time as the drilling fluid is pumped downhole, a cake of solids forms on the wall of the formation as liquid from the drilling fluid filters into the formation. This cake is commonly referred to as a "mud cake." The erodibility of the mud cake is an important consideration for engineers designing and supervising the drilling operations.

Cement compositions and drilling fluids are designed for a variety of wellbore conditions, which may vary in depth, temperature, and pressure. In designing a cement composition or drilling fluid for a wellbore, a number of potential slurries and/or fluids are typically tested in a laboratory for pumpability, safe placement time, compressive strength, filtration rate, erodibility, etc. Ideally, cement compositions and drilling fluids should be analyzed at actual wellbore conditions, such as the wellbore pressure and temperature, and their performance monitored in real time. Existing measurement techniques and apparatuses for measuring cement shrinkage/expansion and erodibility and performing goniometry are not able to achieve measurements in real time at high pressure and high temperature conditions, in situ, or non-invasively.

There continues to be a need for such measurement techniques in order to design cement compositions and drilling fluids suitable for use in a wellbore at particular conditions.

BRIEF DESCRIPTION OF THE DRAWINGS

Illustrative embodiments of the present disclosure are described in detail below with reference to the attached drawing figures, which are incorporated by reference herein and wherein.

Figure 1:
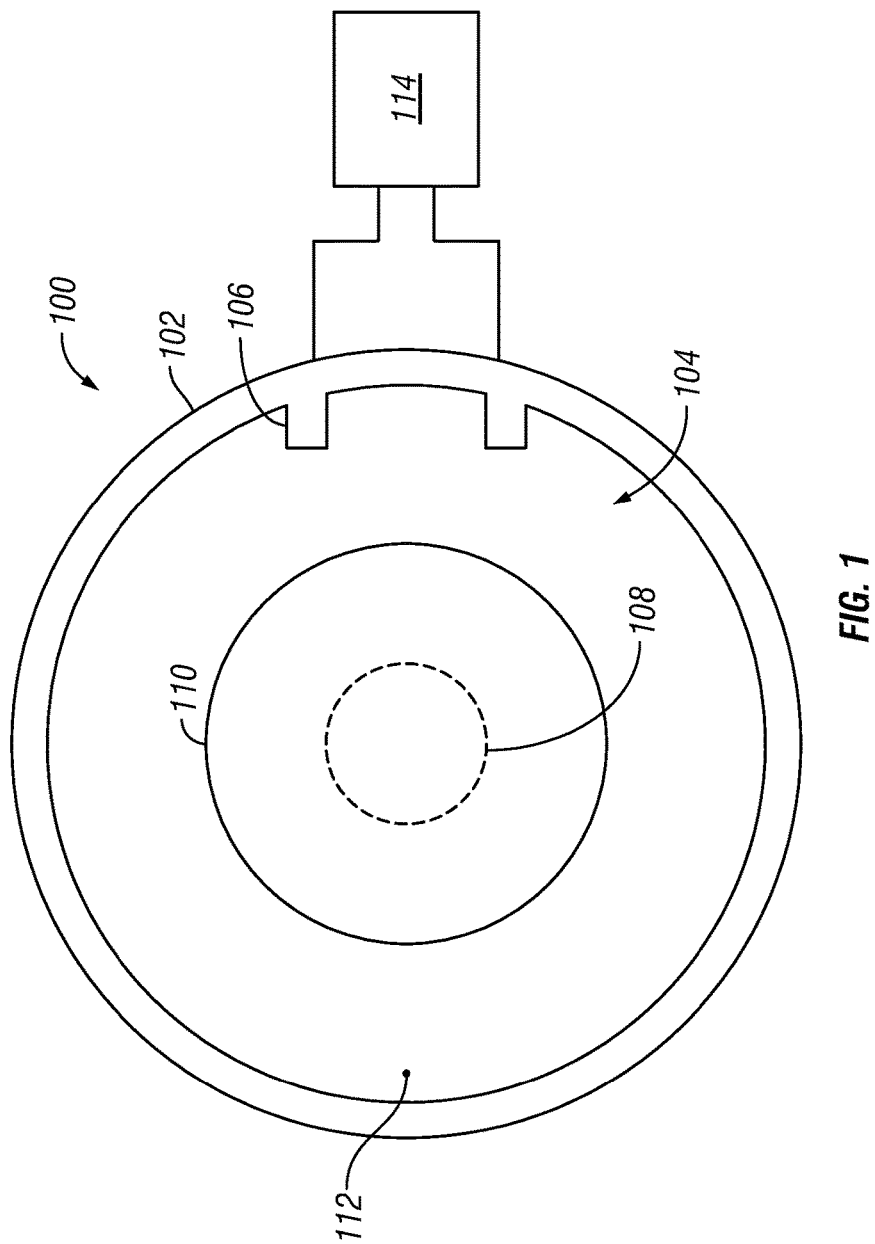
FIG. 1 is a top view of a high pressure high temperature optical measurement system.

The illustrated figures are only exemplary and are not intended to assert or imply any limitation with regard to the environment, architecture, design, or process in which different embodiments may be implemented.

DETAILED DESCRIPTION OF ILLUSTRATIVE EMBODIMENTS

The following discussion is directed to various embodiments of the present disclosure. The drawing figures are not necessarily to scale. Certain features of the embodiments may be shown exaggerated in scale or in somewhat schematic form and some details of conventional elements may not be shown in the interest of clarity and conciseness. Although one or more of these embodiments may be preferred, the embodiments disclosed should not be interpreted, or otherwise used, as limiting the scope of the disclosure, including the claims. It is to be fully recognized that the different teachings of the embodiments discussed below may be employed separately or in any suitable combination to produce desired results. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but are the same structure or function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. In addition, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis. The use of "top," "bottom,"

"above," "below," and variations of these terms is made for convenience, but does not require any particular orientation of the components.

Reference throughout this specification to "one embodiment," "an embodiment," or similar language means that a particular feature, structure, or characteristic described in connection with the embodiment may be included in at least one embodiment of the present disclosure. Thus, appearances of the phrases "in one embodiment," "in an embodiment," and similar language throughout this specification may, but do not necessarily, all refer to the same embodiment.

Now referring to FIG. 1, a top cross-sectional view of an optical measurement system 100 for evaluating performance of a material in a wellbore is shown. The optical measurement system 100 may perform laboratory screening tests for a number of samples to determine performance of the samples in a wellbore. Performance for a wellbore includes performance under conditions simulating, matching, based on, designed for, or otherwise corresponding to those in or expected in the wellbore. The optical measurement system 100 provides for real-time measurement of any dimensional changes occurring in a sample disposed in the system 100, as well as goniometry analyses. In particular, the optical measurement system 100 monitors dimensional changes in a sample via optical means such as optical sensors or cameras.

The optical measurement system 100 illustrated in FIG. 1 comprises a pressure vessel 102 including an internal volume 104. In the illustrated embodiment, the pressure vessel 102 comprises a circular profile and is generally cylindrical in shape with a domed upper portion. However, the pressure vessel 102 can be any geometry suitable for performing measurements of a sample as discussed herein. The pressure vessel 102 includes a thermal element (not shown) capable of providing thermal energy to the system 100 and a pump with a pressure regulator (not shown) capable of pressuring the system 100. Thus, the pressure vessel is capable of achieving high pressure and high temperature conditions that simulate downhole pressure and temperatures.

The optical measurement system 100 further includes optical sensors 106, such as cameras, extending into the internal volume 104 of the pressure vessel 102. Although shown extending into the internal volume 104 of the pressure vessel 102, the optical sensors 106 could also be located external to the pressure vessel 102. The optical sensors are capable of monitoring a sample 110 disposed within the internal volume 104 of the pressure vessel 102. In the illustrated embodiment, two optical sensors 106 are disposed on the side walls of the vessel 102 and provide for monitoring in the plane of the cross section of the vessel 102. These optical sensors 106 provide stereo vision and hence depth perception within the internal volume 104 of the vessel 102. In addition to optical sensors 106, there is another camera 108 disposed in the upper portion of the internal volume 104 of the vessel 102. Camera 108 provides for monitoring of the position of the sample 110 within the internal volume 104 of the vessel 102. Once properly calibrated to account for the properties of the pressurizing fluid and the location of the sample, optical sensors 106 can monitor the sample and detect dimensional changes occurring in the sample in real time and in situ. The measurements are made non-invasively in that the monitoring elements, i.e., the optical sensors 106, do not extend into the internal volume 104 of the vessel 102 and do not interfere with the testing.

The optical measurement system 100 also includes a reference point 112, in this instance a dot, which is located at a known location. The reference point 112 provides for self-calibration of the image processing system 114. Specifically, when there is a change in the refractive index of the material in the internal volume 104 of vessel 102 (e.g., due to change in pressurizing fluid, temperature, etc.), the image processing system can self-calibrate optical sensors 106 by using this reference point 112. Specifically, self-calibration of optical sensors 106 generally proceeds as follows. The vessel 102 is pressurized (e.g., by filling with pressurizing fluid) and heated to a desired temperature (e.g., by a thermal jacket). Then the distance from the reference point 112 to optical sensors 106 is measured using optical sensors 106. The measured distance is compared to the known distance in air. The distance in air is known as it is a system parameter. Where the measured distance differs from the distance in air, the optical sensors 106 are corrected for the refractive index of the fluid in the vessel 102. The image processing system 114 can rely on visible light (450-750 nm) or even wavelengths outside of the visible light range, such as infrared light. When relying on infrared light, the reference dot can be, e.g., an infrared light emitting diode.

Figure 2:
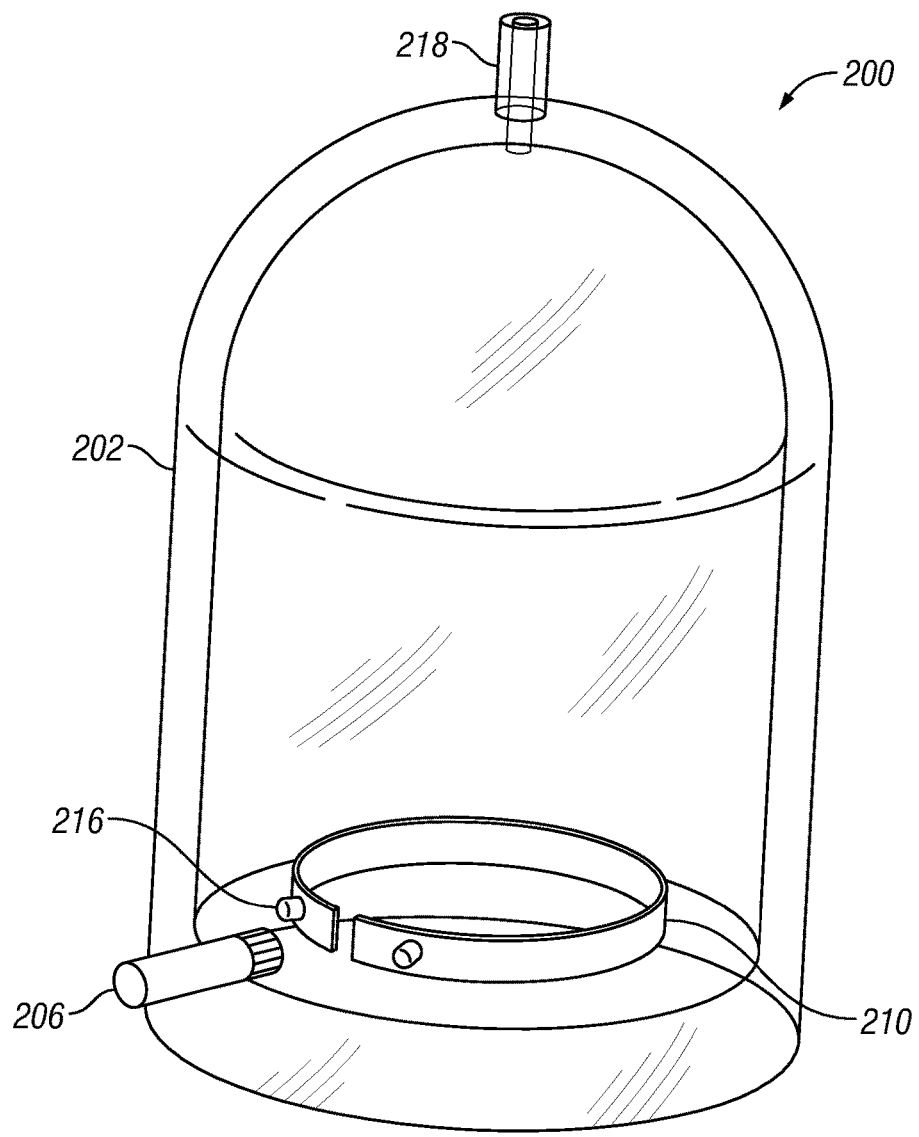
FIG. 2 is a three-dimensional rendering of an optical measurement system for monitoring a cement composition sample.
Figure 3:
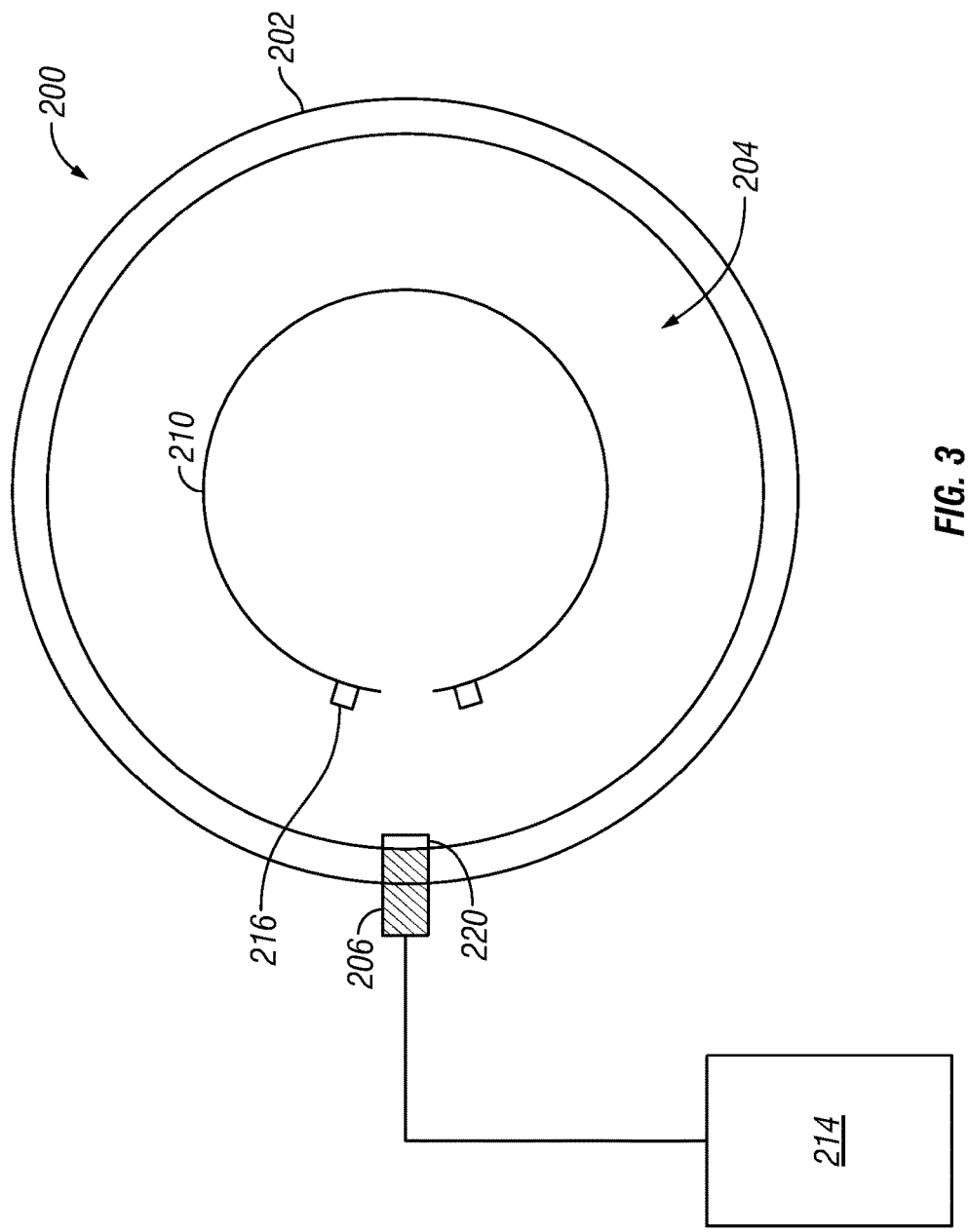
FIG. 3 is a top cross sectional view of the optical measurement system for monitoring a cement composition sample illustrated in FIG. 2.

Now referring to FIGS. 2 and 3, an optical measurement system 200 for evaluating cement shrinkage and/or expansion is shown. FIG. 2 illustrates a three-dimensional rendering of an optical measurement system 200 for evaluating cement shrinkage and/or expansion. FIG. 3 illustrates a top cross-sectional view of the optical measurement system 200 illustrated in FIG. 2.

As discussed above, wet cement slurry is pumped down the wellbore to fill the annular space defined between the casing and the rock walls. The measurement system 200 may perform laboratory screening tests for cement compositions to determine performance of the cement compositions in a wellbore. Performance for a wellbore includes performance under conditions simulating, matching, based on, designed for, or otherwise corresponding to those in or expected in the wellbore. The optical measurement system 200 provides for real-time measurement of any dimensional changes occurring in a sample disposed in the system 200.

The optical measurement system 200 illustrated in FIGS. 2 and 3 comprises a pressure vessel 202 including an internal volume 204. In the illustrated embodiment, the pressure vessel 202 comprises a circular profile and is generally cylindrical in shape with a domed upper portion. However, the pressure vessel 202 can be any geometry suitable for performing measurements of a sample as discussed herein. The pressure vessel 202 includes a thermal element (not shown) capable of providing thermal energy to the system 200 and a pump with a pressure regulator (not shown) capable of pressuring the system 200. The pump pressurizes the vessel 202 by pumping pressurized fluid through port 218. Thus, the pressure vessel is capable of achieving high pressure high temperature conditions that simulate downhole pressure and temperatures.

The optical measurement system 200 also includes an optical sensor 206. In the embodiment illustrated in FIG. 2, the optical sensor 206 is an infrared camera. In alternative embodiments, other suitable cameras could be used, such as a camera for detecting visible light. The optical sensor 206 is disposed on the perimeter of the vessel 202 in a cavity and provides for monitoring in the plane of the cross section of the vessel 202. The wall of the cavity nearest the sample can include a window 220 comprising high strength, transparent material such as toughened glass or the like. Thus, the optical sensor 206 can detect light directed at the window 220 while being protected from the high pressure and high temperature environment in the internal volume 204 of the vessel 202. The optical sensor 206 is configured to detect light emitted from light sources disposed in the internal volume 204 of the vessel 202, discussed in greater detail below.

The optical measurement system 200 further includes a flexible ring mold 210 disposed in the internal volume 104 of the pressure vessel 102. The flexible ring mold 210 is configured to accept a cement composition sample. The ring mold 210 is circular in shape, and comprises two terminals ends not in contact with each other. Disposed on each terminal end is a light source 216. The light source 216 in the illustrated embodiment is an infrared light emitting diode. However, in other embodiments, other light sources can be used, such as a light source emitting visible light. Importantly, the light sources 216 and optical sensor 206 are selected such that the optical sensor 206 can detect the light emitted from the light sources 216. The optical sensor 206 detects light emitted from the light sources 216 in real time.

Figure 4B:
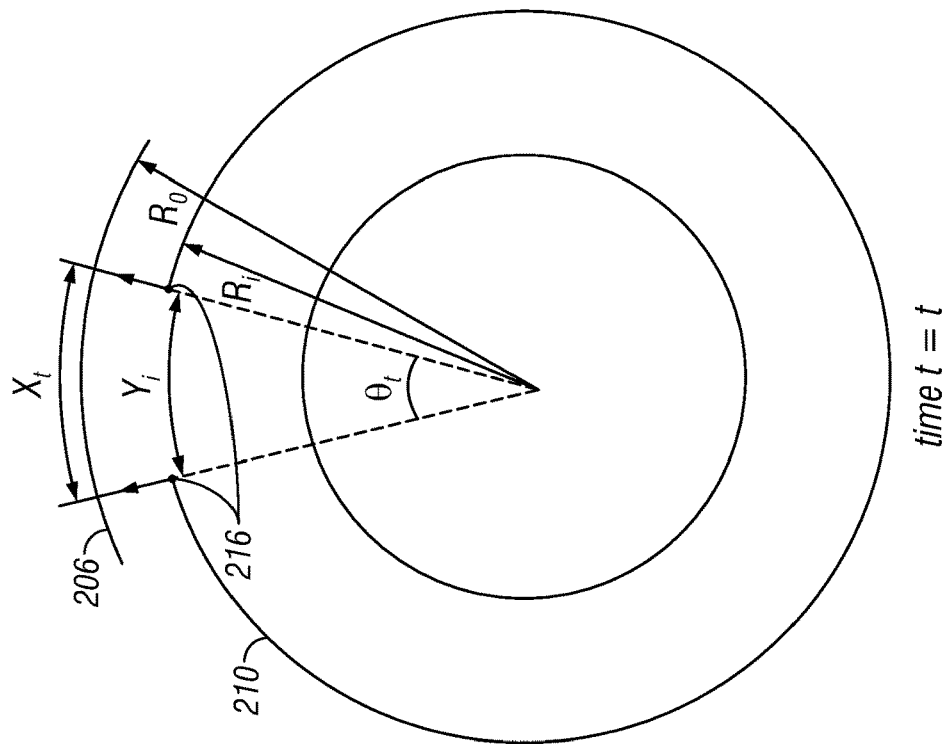
FIGS. 4A and 4B are before and after schematic representations of an optical measurement system for monitoring a cement composition sample.
Figure 4A:
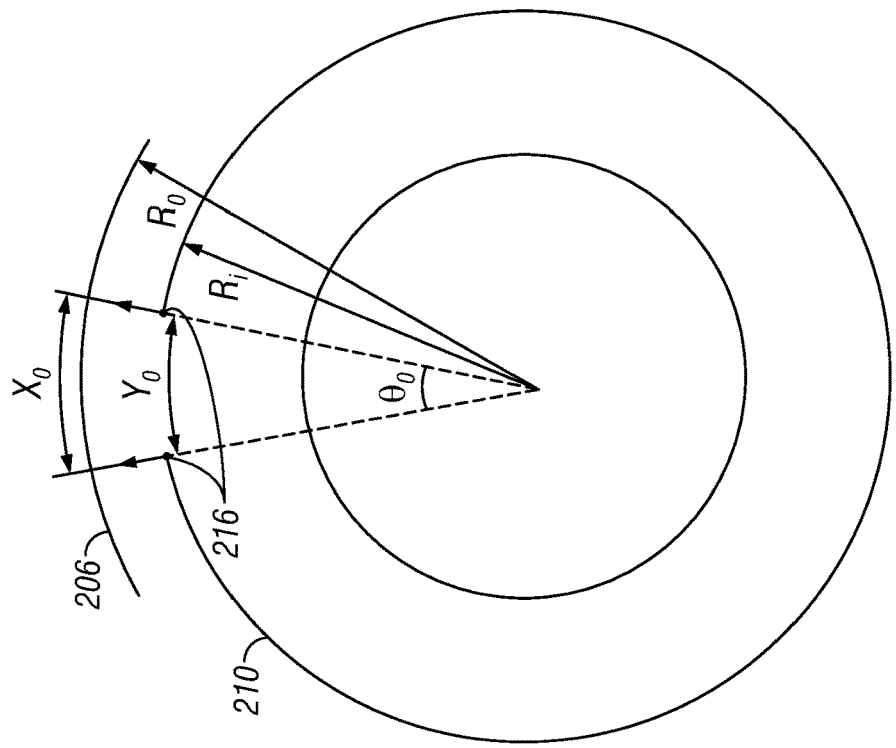

After the cement composition sample is introduced to the flexible ring mold 210, the cement composition sample hydrates and experiences a change in volume. The change in volume of the cement composition sample is evidenced by movement of the terminal positions of the ring mold 210, i.e., if the cement composition sample expands, the gap between the terminal ends will increase, if the cement composition shrinks, the gap between the terminal ends will decrease. Thus, the change is volume is proportional to the actual deviation length of the terminal ends of the ring mold 210. The actual deviation of the terminal ends of the ring mold 210 can be determined by applying the following trigonometric relation with reference to FIGS. 4A and 4B:

$$\tan\theta_o \approx \frac{X_o}{R_o} \approx \frac{Y_o}{R_i} \rightarrow Y_o \approx X_o \frac{R_i}{R_o} \text{ and } Y_t \approx X_t \frac{R_i}{R_o} \quad [1]$$

Where $Y_o$ is the arc length subtended by light sources 216 on the ring mold 210 at time t=0; $X_o$ is the arc length subtended by light sources 216 on the optical sensor 206 at time t=0; $Y_t$ is the arc length subtended by light sources 216 on the ring mold 210 at time t=t; $X_t$ is the arc length subtended by light sources 216 on the optical sensor 206 at time t=t; $R_i$ is the radial distance from the center of the vessel 202 to the light sources 216; $R_o$ is the radial distance from the center of the assembly to the optical sensor 206; $\Theta_o$ is the angle subtended by the light source positions on the optical sensor 206 surface at time t=0; and $\Theta_t$ is the angle subtended by the light source 216 positions on the optical sensor 206 at time t=t.

The optical sensor 206 tracks the movement of the light sources 216 from time t=0 to time t=t in real time. In traditional ring mold testing (i.e., not using optics and not capable of real-time measurements), ring mold deviation is determined after the test is completed by removing the ring mold from the vessel and observing the actual deviation of the terminal ends of the ring mold. This technique cannot be performed in situ and, thus, experimental artifacts can affect the system. The present disclosure, on the other hand, provides for real-time and in-situ monitoring of terminal end deviation at specified pressures and temperatures reflecting downhole conditions.

The change in volume of the cement composition sample is related to the arc length change derived above by the following correlation which is temperature dependent:

% volume change($T>170°$ F.)=$(R_T-R_O)\times 9.095-T\times 3.3E-04$; or [2]

% volume change($T\leq170°$ F.)=$(R_T-R_O)\times 9.095$ [3], where $R_o$=initial arch length; $R_T$=arch length at a given temperature T. By determining the change in volume of the cement composition sample in real time at downhole conditions over a period of time from t=0 to t=t, better cement formulations can be derived to suit the particular formation being drilled, avoiding issues discussed above such as cement failure.

The optical measurement system has applications other than tracking shrinkage and/or expansion of a cement composition sample. For instance, the optical measurement system can be used to examine mud cake erodibility by monitoring, in real time, the volumetric change in a mud cake over a period of time at high pressure and high temperature conditions reflecting downhole conditions. In addition, the optical measurement system can analyze the goniometry of a sample being monitored. Goniometry is particularly important in the context of cementing a well in that adhesion of the cement depends on the goniometry of the surface of the formation and casing. Current laboratory experiments for analyzing the goniometry of a system are unreliable at high pressure and high temperature conditions, such as those experienced downhole.

The disclosed optical measurement system can obtain high resolution determinations of dimensional changes in samples being monitored. Further, potential sources of errors, such as noise, can be minimized through the use of monochromatic sources and specialized cameras.

In addition to the embodiments described above, many examples of specific combinations are within the scope of the disclosure, some of which are detailed below:

Example 1

A measurement system for providing real-time, in-situ measurements of dimensional changes of a sample, comprising:
  a vessel including an internal volume configured to house the sample;
  a means for controlling pressure and temperature in the internal volume of the vessel; and
  an optical sensor configured to monitor dimensional changes in the sample over time and perform goniometry on the sample.

Example 2

The system of example 1, further comprising an optical sensor disposed on top of the vessel and configured to monitor the position of the sample within the internal volume of the vessel.

Example 3

The system of example 1, further comprising a plurality of optical sensors.

Example 4

The system of example 3, wherein the optical sensors are disposed about the perimeter of the vessel.

Example 5

The system of example 4, further comprising:
  a reference point; and an image processing system,
wherein the optical sensors are configured to be self-calibrating with regard to the reference point by the image processing system.

Example 6

The system of example 1, further comprising a circular flexible ring mold capable of expanding and contracting and disposed within the internal volume of the vessel, wherein the ring mold is disposed around the sample.

Example 7

The system of example 6, wherein the ring mold comprises light sources being detectable by the optical sensor.

Example 8

The system of example 7, wherein deviation of the light sources over time is indicative of volumetric change of the sample over time.

Example 9

The system of example 1, wherein the sample is cement.

Example 10

The system of example 1, wherein the sample is a mud cake.

Example 11

A method for performing real-time, in-situ optical measurements of a sample material for use in a wellbore comprising:
disposing the sample material in a vessel;
adjusting the pressure and temperature in the vessel to a desired pressure and temperature; and
monitoring the sample at the desired pressure and temperature via an optical sensor over a desired period of time.

Example 12

The method of example 11, wherein the desired temperature and pressure are based on downhole conditions in a wellbore.

Example 13

The method of example 11, further comprising determining dimensional changes in the sample over the period of time based on the monitoring.

Example 14

The method of example 11, further comprising calibrating the optical sensor with regard to a reference point disposed in the vessel.

Example 15

The method of example 11, further comprising a circular flexible ring mold capable of expanding and contracting disposed within the internal volume of the vessel, wherein the sample is disposed within the ring mold.

Example 16

The method of example 15, the ring mold further comprising light sources being detectable by the optical sensor.

Example 17

The method of example 16, further comprising:
measuring the actual deviation of the light sources over time; and
calculating the volumetric change of the sample based on the deviation of the light sources.

Example 18

The method of example 11, wherein the sample is cement.

Example 19

The method of example 11, wherein the sample is a mud cake.

Example 20

The method of example 11, further comprising performing goniometry on the sample.

While the aspects of the present disclosure may be susceptible to various modifications and alternative forms, specific embodiments have been shown by way of example in the drawings and have been described in detail herein. But it should be understood that the invention is not intended to be limited to the particular forms disclosed. Rather, the invention is to cover all modifications, equivalents, and alternatives falling within the spirit and scope of the invention as defined by the following appended claims.

We claim:

1. A measurement system for providing real-time, in-situ measurements of dimensional changes of a sample, comprising:
a vessel including an internal volume configured to house the sample;
a means for controlling pressure and temperature in the internal volume of the vessel; and
an optical sensor configured to monitor dimensional changes in the sample over time and perform goniometry on the sample.

2. The system of claim 1, further comprising an optical sensor disposed on top of the vessel and configured to monitor the position of the sample within the internal volume of the vessel.

3. The system of claim 1, further comprising a plurality of optical sensors.

4. The system of claim 3, wherein the optical sensors are disposed about the perimeter of the vessel.

5. The system of claim 4, further comprising:
a reference point; and
an image processing system,
wherein the optical sensors are configured to be self-calibrating with regard to the reference point by the image processing system.

6. The system of claim 1, further comprising a circular flexible ring mold capable of expanding and contracting and disposed within the internal volume of the vessel, wherein the ring mold is disposed around the sample.

7. The system of claim 6, wherein the ring mold comprises light sources being detectable by the optical sensor.

8. The system of claim 7, wherein deviation of the light sources over time is indicative of volumetric change of the sample over time.

9. The system of claim 1, wherein the sample is cement.

10. The system of claim 1, wherein the sample is a mud cake.

11. A method for performing real-time, in-situ optical measurements of a sample material for use in a wellbore comprising:
disposing the sample material in a vessel;
adjusting the pressure and temperature in the vessel to a desired pressure and temperature; and
monitoring the sample at the desired pressure and temperature via an optical sensor over a desired period of time to perform goniometry on the sample.

12. The method of claim 11, wherein the desired temperature and pressure are based on downhole conditions in a wellbore.

13. The method of claim 11, further comprising determining dimensional changes in the sample over the period of time based on the monitoring.

14. The method of claim 11, further comprising calibrating the optical sensor with regard to a reference point disposed in the vessel.

15. The method of claim 11, further comprising a circular flexible ring mold capable of expanding and contracting disposed within the internal volume of the vessel, wherein the sample is disposed within the ring mold.

16. The method of claim 15, the ring mold further comprising light sources being detectable by the optical sensor.

17. The method of claim 16, further comprising:
measuring the actual deviation of the light sources over time; and
calculating the volumetric change of the sample based on the deviation of the light sources.

18. The method of claim 11, wherein the sample is cement.

19. The method of claim 11, wherein the sample is a mud cake.

20. The method of claim 16, further comprising performing goniometry on the sample by monitoring a position of the light sources.

* * * * *